United States Patent [19]

Melgoza

[11] Patent Number: Plant 6,825

[45] Date of Patent: May 30, 1989

[54] BARCELO YELLOW CARPET

[75] Inventor: Rafael Melgoza, Ontario, Calif.

[73] Assignee: Barcelo Plant Growers, Inc., Brea, Calif.

[21] Appl. No.: 78,867

[22] Filed: Jul. 28, 1987

[51] Int. Cl.[4] ..... A01H 5/00

[52] U.S. Cl. ..... Plt./68

[58] Field of Search ..... Plt./68

[56] References Cited

U.S. PATENT DOCUMENTS

P.P. 5,795 11/1986 Ono ..... Plt. 68

*Primary Examiner*—James R. Feyrer

*Attorney, Agent, or Firm*—Lyon & Lyon

[57] ABSTRACT

A new and distinct type of Gazania characterized by its semi-trailing growth pattern and flower color, particularly adapted for use as an ornamental ground cover.

2 Drawing Sheets

BACKGROUND

The present invention relates to a new and distinct variety of *Gazania rigens leucolaena,* the novel characteristics of which reside particularly in the color patterns of the ray flowers and disk flowers and the semi-trailing growth pattern.

The new Gazania was first discovered by me in 1986. It originated as a mutant from a hybrid of Gazania known as "Orange Trailing", in a cultivated garden in Brea, Calif. Thereafter the new variety was successfully asexually reproduced by myself by rooting cuttings. Such asexual reproduction resulted in numerous progeny plants which have continually displayed the flower color and growth pattern typical of that found on the parent mutant.

An interesting characteristic of the new variety is the yellow, daisy-like flower approximately two inches in diameter. The flower is comprised of lemon chrome, plate IV, hue 21, on Ridgeway's color plates (hereinafter "R") ray flowers with a black oval spot at the base of each petal, which oval contains a small white rectangularly-shaped dot near the top of the oval, and lemon chrome, plate IV, hue 21 (R), disk flowers at the center of the inflorescence. Another interesting characteristic is the semi-trailing growth pattern of this plant which spreads by trailing stems but remains fairly dense in its coverage of the ground.

The new variety, as compared with the "Orange Trailing" hybrid of *Gazania rigens leucolaena,* is characterized by its bright yellow flower, compared to the orange flower of the known variety, and by its semi-trailing growth pattern, compared to the extended trailing growth pattern of the known variety. The known variety and the new variety each possess the characteristic black oval spot at the base of each petal, which oval contains a small, white, rectangularly-shaped dot.

BRIEF DESCRIPTION OF THE DRAWINGS

Other distinctive characteristics of the new variety are exemplified in the accompanying illustrations.

TECHNICAL DESCRIPTION

Figure 1:
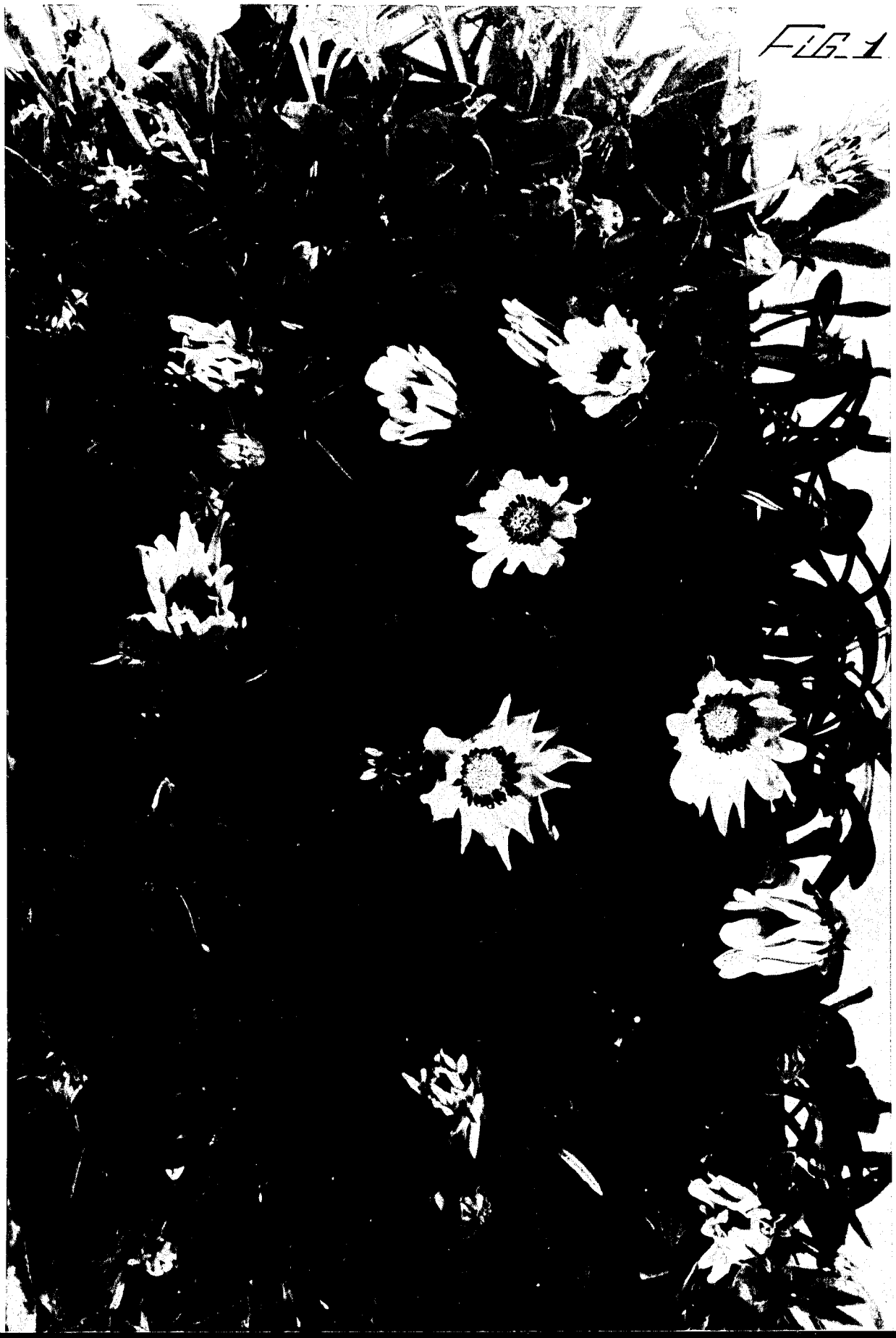
FIG. 1 is a close up of the inflorescence of several adult plants.
Figure 2:
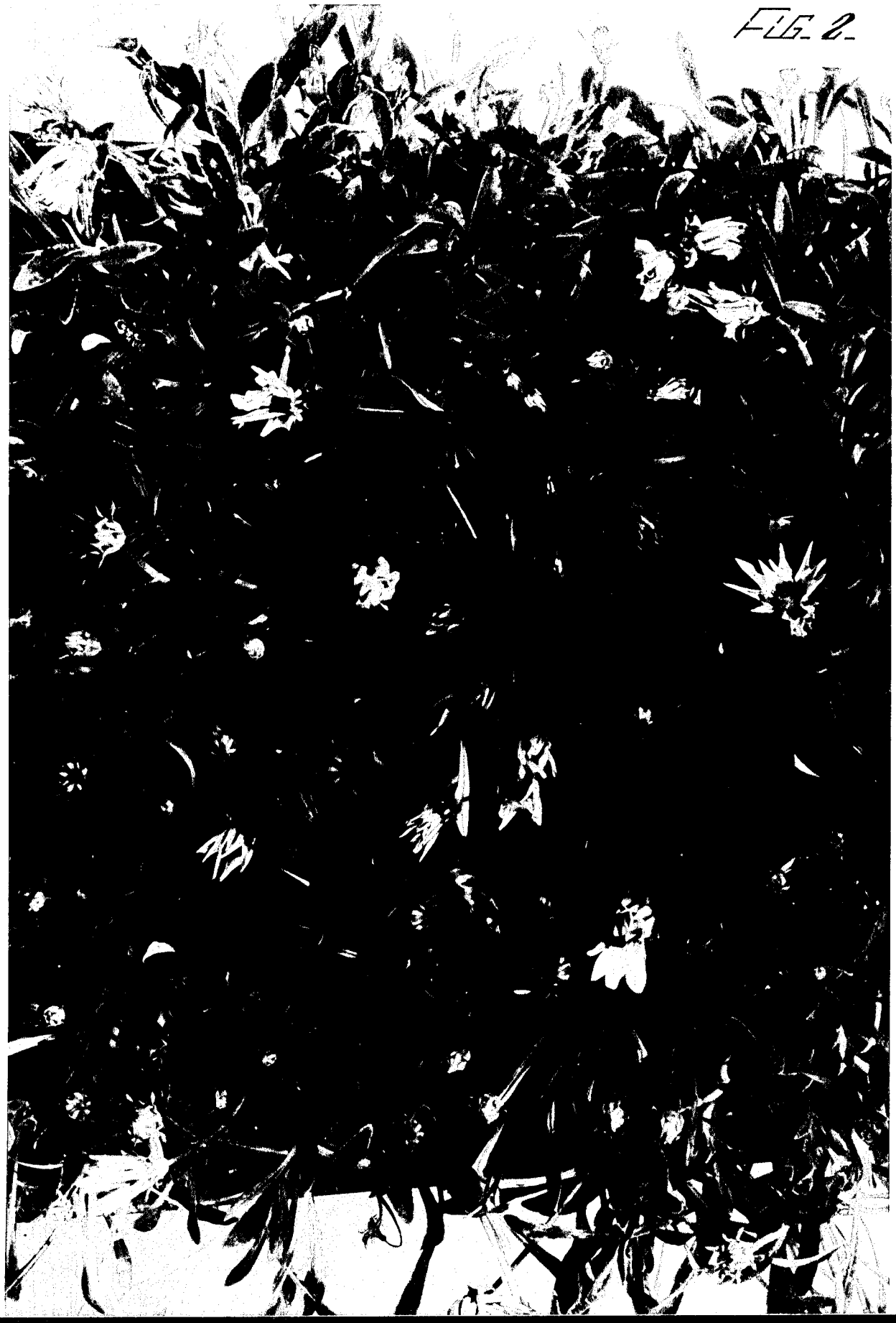
FIG. 2 shows a number of mature specimens in a flat.

The following is a description in some detail of the new variety of *Gazania rigens leucolaena,* Gazania yellow carpet.

FLOWER

Blooming habit: In climate of Southern California, blooms continuously throughout the year; blooms profusely late in spring and early summer.

Bud: Large size, pointed, not affected by wet weather or hot weather. Color is pale green when sepals first divide and turns to dark brown and then light yellow as petals begin to unfurl. Sepals have smooth edges and curl back immediately upon dividing. Calyx is large size, pear-shaped, hairy aspect. Peduncle is long and bending, rough aspect, light green color.

Bloom: Large size approximately 2 inches in diameter, long and bending stems, borne singly, composite, radiate head. Mature heads radiate, with 14–19 ray flowers and numerous disk flowers. Heads marcescent. No fragrance. Petals fall off cleanly when whole flower dies.

Ray flowers: liguate with entire strap-shaped limb. Color: lemon chrome, plate IV, hue 21 (R) at blooming and maintains color through maturity; outside of approximately every other petal contains black striation traveling the length of the petal, which striation fades upon maturity.

Disk Flowers: regular and funnel form.

*Color.*—Lemon chrome, plate IV, hue 21(R).

FOLIAGE

Form and growth: Semi–Trailing ground cover, vigorous, dense growth usually observed in clumping varieties.

Leaves: Color is bright green on top of leaf and silver-grey on bottom of leaf, long, slender at base and spatulate towards tip, velvety on top of leaf and rough underneath leaf, smooth edge.

Other characteristics: Will tolerate considerable drought and wind conditions; resistant to humidity-induced fungus.

Season perennial.

The above described new variety of Gazania displays an attractive color pattern and semi-trailing growth pattern making it an excellent ornamental ground cover useful on banks, level ground or in hanging baskets.

I claim:

1. A new and distinct variety of *Gazania rigens leucolaena* as described and shown herein characterized particularly by its vigorous semi-trailing growth pattern and by its yellow ray flowers with yellow centers, as compared with the "Orange Trailing" variety.

* * * * *